US010342662B2

(12) United States Patent  
O'Neil et al.

(10) Patent No.: US 10,342,662 B2  
(45) Date of Patent: Jul. 9, 2019

(54) ASPIRATING IMPLANTS AND METHOD OF BONY REGENERATION

(71) Applicant: DePuy Synthes Products, Inc., Raynham, MA (US)

(72) Inventors: Michael J. O'Neil, West Barnstable, MA (US); Liesbeth Brown, West Newton, MA (US); Nimish Parikh, Boulder, CO (US); Daniel Keeley, Rochester, NY (US); Shannon Cormier, Newburyport, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/721,090

(22) Filed: Sep. 29, 2017

(65) Prior Publication Data

US 2018/0085220 A1    Mar. 29, 2018

Related U.S. Application Data

(63) Continuation of application No. 15/218,210, filed on Jul. 25, 2016, now Pat. No. 9,801,725, which is a (Continued)

(51) Int. Cl.
*A61F 2/44* (2006.01)
*A61F 2/28* (2006.01)
(Continued)

(52) U.S. Cl.
CPC ........ *A61F 2/2846* (2013.01); *A61B 17/8805* (2013.01); *A61B 17/8841* (2013.01); (Continued)

(58) Field of Classification Search
CPC ................................................ A61F 2/44–447
See application file for complete search history.

(56) References Cited

U.S. PATENT DOCUMENTS 2,115,250 A    4/1938    Bruson
2,170,111 A    8/1939    Bruson
(Continued)

FOREIGN PATENT DOCUMENTS

DE    197 10 392 C1    7/1999
WO    93/17669 A1    9/1993
(Continued)

OTHER PUBLICATIONS

[No Author Listed] Cervios and Cervios chromos Radiolucent cage system for anterior cervical interbody fusion, Technique Guide, 32 pages, Synthes, 2007.
(Continued)

*Primary Examiner* — Nicholas J Plionis
(74) *Attorney, Agent, or Firm* — Nutter McClennen & Fish LLP

(57) ABSTRACT

Devices and methods for in situ drawing, filtering and seeding cells from the marrow of surrounding bone into a fusion cage without any of the challenges mentioned above. Various implants and devices with aspiration ports that enable in-situ harvesting and mixing of stem cells. These devices may include spinal fusion cages, long bone spacers, lateral grafts and joint replacement devices. Each device utilizes at least one aspiration port for harvesting of stem cell-containing marrow via aspiration from adjacent bony elements.

16 Claims, 16 Drawing Sheets

Related U.S. Application Data continuation of application No. 14/877,901, filed on Oct. 7, 2015, now abandoned, which is a continuation of application No. 12/634,647, filed on Dec. 9, 2009, now Pat. No. 9,168,138.

(51) Int. Cl.
  *A61F 2/46* (2006.01)
  *A61B 17/88* (2006.01)
  *A61F 2/30* (2006.01)

(52) U.S. Cl.
  CPC ............... *A61F 2/28* (2013.01); *A61F 2/441* (2013.01); *A61F 2/447* (2013.01); *A61F 2/4455* (2013.01); *A61F 2/4465* (2013.01); *A61F 2/4611* (2013.01); *A61F 2/4644* (2013.01); *A61F 2/30965* (2013.01); *A61F 2002/285* (2013.01); *A61F 2002/2817* (2013.01); *A61F 2002/2832* (2013.01); *A61F 2002/2842* (2013.01); *A61F 2002/2867* (2013.01); *A61F 2002/30062* (2013.01); *A61F 2002/3068* (2013.01); *A61F 2002/30224* (2013.01); *A61F 2002/30588* (2013.01); *A61F 2002/30677* (2013.01); *A61F 2002/30841* (2013.01); *A61F 2002/4648* (2013.01); *A61F 2002/4685* (2013.01); *A61F 2310/00017* (2013.01); *A61F 2310/00023* (2013.01); *A61F 2310/00029* (2013.01); *A61F 2310/00203* (2013.01); *A61F 2310/00239* (2013.01)

(56) References Cited

U.S. PATENT DOCUMENTS

| | | | |
|---|---|---|---|
| 2,229,024 | A | 1/1941 | Bruson |
| 2,706,701 | A | 4/1955 | Beller et al. |
| 2,710,277 | A | 6/1955 | Shelanski et al. |
| 2,826,532 | A | 3/1958 | Hosmer |
| 2,900,305 | A | 8/1959 | Siggia |
| 2,977,315 | A | 3/1961 | Scheib et al. |
| 3,228,828 | A | 1/1966 | Romano |
| 3,717,655 | A | 2/1973 | Godefroi et al. |
| 3,867,728 | A * | 2/1975 | Stubstad ............ A61F 2/30907 128/DIG. 21 |
| 4,352,883 | A | 10/1982 | Lim |
| 4,440,921 | A | 4/1984 | Allcock et al. |
| 4,495,174 | A | 1/1985 | Allcock et al. |
| 4,645,503 | A | 2/1987 | Lin et al. |
| 4,651,717 | A | 3/1987 | Jakubczak |
| 4,743,256 | A | 5/1988 | Brantigan |
| 4,772,287 | A | 9/1988 | Ray et al. |
| 4,863,476 | A | 9/1989 | Shepperd |
| 4,880,622 | A | 11/1989 | Allcock et al. |
| 4,932,969 | A | 6/1990 | Frey et al. |
| 5,059,193 | A | 10/1991 | Kuslich |
| 5,123,926 | A | 6/1992 | Pisharodi |
| 5,133,755 | A | 7/1992 | Brekke |
| 5,192,327 | A | 3/1993 | Brantigan |
| 5,348,391 | A * | 9/1994 | Murray ............... B01F 7/00208 366/139 |
| 5,374,267 | A | 12/1994 | Siegal |
| 5,390,683 | A | 2/1995 | Pisharodi |
| 5,397,364 | A | 3/1995 | Kozak et al. |
| 5,410,016 | A | 4/1995 | Hubbell et al. |
| 5,443,514 | A | 8/1995 | Steffee |
| 5,522,895 | A | 6/1996 | Mikos |
| 5,522,899 | A | 6/1996 | Michelson |
| 5,549,679 | A | 8/1996 | Kuslich |
| 5,562,736 | A | 10/1996 | Ray et al. |
| 5,658,335 | A | 8/1997 | Allen |
| 5,665,122 | A | 9/1997 | Kambin |
| 5,679,723 | A | 10/1997 | Cooper et al. |
| 5,702,449 | A | 12/1997 | McKay |
| 5,782,832 | A | 7/1998 | Larsen et al. |
| 5,800,549 | A | 9/1998 | Bao et al. |
| 5,807,327 | A | 9/1998 | Green et al. |
| 5,824,084 | A | 10/1998 | Muschler |
| 5,833,657 | A | 11/1998 | Reinhardt et al. |
| 5,837,752 | A | 11/1998 | Shastri et al. |
| 5,860,973 | A | 1/1999 | Michelson |
| 5,865,848 | A | 2/1999 | Baker |
| 5,888,220 | A | 3/1999 | Felt et al. |
| 5,888,227 | A | 3/1999 | Cottle |
| 5,972,385 | A | 10/1999 | Liu et al. |
| 5,985,307 | A | 11/1999 | Hanson et al. |
| 6,001,130 | A | 12/1999 | Bryan et al. |
| 6,045,579 | A | 4/2000 | Hochshuler et al. |
| 6,049,026 | A | 4/2000 | Muschler |
| 6,071,982 | A | 6/2000 | Wise et al. |
| 6,102,950 | A | 8/2000 | Vaccaro |
| 6,113,624 | A | 9/2000 | Bezwada et al. |
| 6,113,638 | A | 9/2000 | Williams et al. |
| 6,117,174 | A | 9/2000 | Nolan |
| 6,126,689 | A | 10/2000 | Brett |
| 6,129,763 | A | 10/2000 | Chauvin et al. |
| 6,147,135 | A | 11/2000 | Yuan et al. |
| 6,165,486 | A | 12/2000 | Marra et al. |
| 6,171,610 | B1 | 1/2001 | Vacanti et al. |
| 6,176,882 | B1 | 1/2001 | Biedermann et al. |
| 6,187,043 | B1 | 2/2001 | Ledergerber |
| 6,187,048 | B1 | 2/2001 | Milner et al. |
| 6,193,757 | B1 | 2/2001 | Foley et al. |
| 6,197,325 | B1 | 3/2001 | MacPhee et al. |
| 6,203,565 | B1 | 3/2001 | Bonutti et al. |
| 6,214,368 | B1 | 4/2001 | Lee et al. |
| 6,217,579 | B1 | 4/2001 | Koros |
| 6,224,631 | B1 | 5/2001 | Kohrs |
| 6,224,894 | B1 | 5/2001 | Jamiolkowski et al. |
| 6,248,131 | B1 | 6/2001 | Felt et al. |
| 6,264,695 | B1 | 7/2001 | Stoy |
| 6,277,149 | B1 | 8/2001 | Boyle et al. |
| 6,280,474 | B1 | 8/2001 | Cassidy et al. |
| 6,306,177 | B1 | 10/2001 | Felt et al. |
| 6,331,312 | B1 | 12/2001 | Lee et al. |
| 6,332,894 | B1 | 12/2001 | Stalcup et al. |
| 6,352,555 | B1 | 3/2002 | Dzau et al. |
| 6,368,325 | B1 | 4/2002 | McKinley et al. |
| 6,368,351 | B1 | 4/2002 | Glenn et al. |
| 6,375,682 | B1 | 4/2002 | Fleischmann et al. |
| 6,387,130 | B1 | 5/2002 | Stone et al. |
| 6,413,278 | B1 | 7/2002 | Marchosky |
| 6,419,705 | B1 | 7/2002 | Erickson |
| 6,436,140 | B1 | 8/2002 | Liu et al. |
| 6,443,989 | B1 | 9/2002 | Jackson |
| 6,454,807 | B1 | 9/2002 | Jackson |
| 6,478,800 | B1 | 11/2002 | Fraser et al. |
| 6,491,724 | B1 | 12/2002 | Ferree |
| 6,494,883 | B1 | 12/2002 | Ferree |
| 6,558,424 | B2 | 5/2003 | Thalgott |
| 6,562,072 | B1 | 5/2003 | Fuss et al. |
| 6,562,074 | B2 | 5/2003 | Gerbec et al. |
| 6,582,431 | B1 | 6/2003 | Ray |
| 6,592,625 | B2 | 7/2003 | Cauthen |
| 6,595,998 | B2 | 7/2003 | Johnson et al. |
| 6,610,094 | B2 | 8/2003 | Husson |
| 6,632,235 | B2 | 10/2003 | Weikel et al. |
| 6,652,592 | B1 | 11/2003 | Grooms et al. |
| 6,660,038 | B2 | 12/2003 | Boyer, II et al. |
| 6,685,742 | B1 | 2/2004 | Jackson |
| 6,733,535 | B2 | 5/2004 | Michelson |
| 6,755,841 | B2 | 6/2004 | Fraser et al. |
| 6,805,697 | B1 | 10/2004 | Helm et al. |
| 6,835,208 | B2 | 12/2004 | Marchosky |
| 6,852,095 | B1 * | 2/2005 | Ray .................... A61B 17/7097 604/93.01 |
| 6,969,405 | B2 | 11/2005 | Suddaby |
| 6,979,352 | B2 | 12/2005 | Reynolds |
| 6,979,353 | B2 | 12/2005 | Bresina |
| 7,066,960 | B1 * | 6/2006 | Dickman ................. A61F 2/441 623/13.11 |
| 7,326,248 | B2 | 2/2008 | Michelson |
| 7,500,991 | B2 | 3/2009 | Bartish, Jr. et al. |

(56) References Cited

U.S. PATENT DOCUMENTS

| | | |
|---|---|---|
| 7,503,920 B2 | 3/2009 | Siegal |
| 7,618,458 B2 | 11/2009 | Biedermann et al. |
| 7,655,010 B2 | 2/2010 | Serhan et al. |
| 7,666,266 B2 | 2/2010 | Izawa et al. |
| 7,670,374 B2 | 3/2010 | Schaller |
| 7,703,727 B2 | 4/2010 | Selness |
| 7,785,368 B2 | 8/2010 | Schaller |
| 7,799,081 B2 | 9/2010 | McKinley |
| 7,837,734 B2 | 11/2010 | Zucherman et al. |
| 7,850,733 B2 | 12/2010 | Baynham et al. |
| 7,918,874 B2 | 4/2011 | Siegal |
| 7,935,051 B2 | 5/2011 | Miles et al. |
| 7,942,903 B2 | 5/2011 | Moskowitz et al. |
| 7,947,078 B2 | 5/2011 | Siegal |
| 8,007,535 B2 | 8/2011 | Hudgins et al. |
| 8,057,544 B2 | 11/2011 | Schaller |
| 8,206,423 B2 | 6/2012 | Siegal |
| 8,236,029 B2 | 8/2012 | Siegal |
| 8,241,328 B2 | 8/2012 | Siegal |
| 8,246,622 B2 | 8/2012 | Siegal et al. |
| 8,328,812 B2 | 12/2012 | Siegal et al. |
| 8,343,193 B2 | 1/2013 | Johnson et al. |
| 8,382,842 B2 | 2/2013 | Greenhalgh et al. |
| 8,403,990 B2 | 3/2013 | Dryer et al. |
| 8,454,617 B2 | 6/2013 | Schaller et al. |
| 8,465,524 B2 | 6/2013 | Siegal |
| 8,486,109 B2 | 7/2013 | Siegal |
| 8,491,591 B2 | 7/2013 | Fuerderer |
| 8,579,981 B2 | 11/2013 | Lim et al. |
| 8,597,330 B2 | 12/2013 | Siegal |
| 8,672,977 B2 | 3/2014 | Siegal et al. |
| 8,777,993 B2 | 7/2014 | Siegal et al. |
| 8,845,638 B2 | 9/2014 | Siegal et al. |
| 8,845,734 B2 | 9/2014 | Weiman |
| 8,900,235 B2 | 12/2014 | Siegal |
| 8,906,098 B2 | 12/2014 | Siegal |
| 8,926,704 B2 | 1/2015 | Glerum et al. |
| 8,986,388 B2 | 3/2015 | Siegal et al. |
| 9,017,408 B2 | 4/2015 | Siegal et al. |
| 9,017,413 B2 | 4/2015 | Siegal et al. |
| 9,044,334 B2 | 6/2015 | Siegal et al. |
| 9,168,138 B2 | 10/2015 | O'Neil et al. |
| 9,254,138 B2 | 2/2016 | Siegal et al. |
| 9,283,092 B2 | 3/2016 | Siegal et al. |
| 9,333,091 B2 | 5/2016 | DiMauro |
| 9,408,712 B2 | 8/2016 | Siegal et al. |
| 9,439,776 B2 | 9/2016 | DiMauro et al. |
| 9,439,777 B2 | 9/2016 | DiMauro |
| 9,801,725 B2 | 10/2017 | O'Neil et al. |
| 2001/0008980 A1 | 7/2001 | Gresser et al. |
| 2001/0039452 A1 | 11/2001 | Zucherman et al. |
| 2001/0039453 A1 | 11/2001 | Gresser et al. |
| 2002/0029084 A1 | 3/2002 | Paul et al. |
| 2002/0045904 A1 | 4/2002 | Fuss et al. |
| 2002/0055781 A1 | 5/2002 | Sazy |
| 2002/0058947 A1 | 5/2002 | Hochschuler et al. |
| 2002/0072801 A1 | 6/2002 | Michelson |
| 2002/0077701 A1 | 6/2002 | Kuslich |
| 2002/0107573 A1 | 8/2002 | Steinberg |
| 2002/0173796 A1 | 11/2002 | Cragg |
| 2002/0193883 A1 | 12/2002 | Wironen |
| 2002/0198526 A1 | 12/2002 | Shaolian et al. |
| 2003/0028251 A1 | 2/2003 | Mathews |
| 2003/0073998 A1 | 4/2003 | Pagliuca et al. |
| 2003/0135275 A1 | 7/2003 | Garcia et al. |
| 2003/0139812 A1 | 7/2003 | Garcia et al. |
| 2003/0199979 A1 | 10/2003 | McGuckin |
| 2004/0002761 A1 | 1/2004 | Rogers et al. |
| 2004/0049270 A1 | 3/2004 | Gewirtz |
| 2004/0087947 A1 | 5/2004 | Lim et al. |
| 2004/0116997 A1 | 6/2004 | Taylor et al. |
| 2004/0117022 A1 | 6/2004 | Marnay et al. |
| 2004/0127990 A1 | 7/2004 | Bartish, Jr. et al. |
| 2004/0193270 A1* | 9/2004 | DiMauro .............. A61F 2/447 623/17.11 |
| 2004/0220669 A1 | 11/2004 | Studer |
| 2004/0225360 A1 | 11/2004 | Malone |
| 2004/0230309 A1 | 11/2004 | DiMauro et al. |
| 2005/0065609 A1 | 3/2005 | Wardlaw |
| 2005/0119752 A1 | 6/2005 | Williams et al. |
| 2005/0124969 A1 | 6/2005 | Fitzgerald et al. |
| 2005/0125062 A1 | 6/2005 | Biedermann et al. |
| 2005/0154460 A1 | 7/2005 | Yundt |
| 2005/0261682 A1 | 11/2005 | Ferree |
| 2006/0036241 A1 | 2/2006 | Siegal |
| 2006/0095135 A1 | 5/2006 | Kovacevic |
| 2006/0122701 A1 | 6/2006 | Kiester |
| 2006/0129244 A1 | 6/2006 | Ensign |
| 2006/0142858 A1 | 6/2006 | Colleran et al. |
| 2007/0100452 A1 | 5/2007 | Prosser |
| 2007/0142916 A1 | 6/2007 | Olson et al. |
| 2007/0179459 A1 | 8/2007 | Geisler et al. |
| 2007/0270956 A1* | 11/2007 | Heinz ................ A61F 2/44 623/17.11 |
| 2008/0077243 A1 | 3/2008 | Lee et al. |
| 2008/0154377 A1 | 6/2008 | Voellmicke |
| 2008/0161927 A1 | 7/2008 | Savage et al. |
| 2008/0172128 A1 | 7/2008 | Perez-Cruet et al. |
| 2008/0188945 A1 | 8/2008 | Boyce et al. |
| 2009/0138015 A1* | 5/2009 | Conner .............. A61B 17/1615 606/80 |
| 2010/0174243 A1 | 7/2010 | McKay |
| 2010/0268343 A1 | 10/2010 | Dewey et al. |
| 2011/0098818 A1 | 4/2011 | Brodke et al. |
| 2011/0137418 A1 | 6/2011 | O'Neil et al. |
| 2012/0310352 A1 | 12/2012 | DiMauro et al. |
| 2013/0190875 A1 | 7/2013 | Shulock et al. |
| 2014/0046446 A1 | 2/2014 | Robinson |
| 2015/0094812 A1 | 4/2015 | Cain |
| 2015/0112437 A1 | 4/2015 | Davis et al. |
| 2015/0164655 A1 | 6/2015 | DiMauro |
| 2015/0173914 A1 | 6/2015 | DiMauro et al. |
| 2015/0196401 A1 | 7/2015 | DiMauro et al. |
| 2015/0202052 A1 | 7/2015 | DiMauro |
| 2015/0216673 A1 | 8/2015 | DiMauro |
| 2016/0000577 A1 | 1/2016 | DiMauro |
| 2016/0022437 A1 | 1/2016 | Kelly et al. |
| 2016/0038304 A1 | 2/2016 | Aquino Shluzas et al. |
| 2016/0051376 A1 | 2/2016 | Serhan et al. |
| 2016/0058573 A1 | 3/2016 | DiMauro et al. |
| 2016/0081804 A1 | 3/2016 | O'Neil et al. |
| 2016/0199196 A1 | 7/2016 | Serhan et al. |
| 2016/0310296 A1 | 10/2016 | DiMauro et al. |
| 2016/0317313 A1 | 11/2016 | DiMauro |
| 2016/0317714 A1 | 11/2016 | DiMauro et al. |
| 2016/0331541 A1 | 11/2016 | DiMauro et al. |
| 2016/0331548 A1 | 11/2016 | DiMauro et al. |
| 2016/0338854 A1 | 11/2016 | Serhan et al. |
| 2016/0367380 A1 | 12/2016 | DiMauro |
| 2016/0374821 A1 | 12/2016 | DiMauro et al. |
| 2017/0049572 A1 | 2/2017 | O'Neil et al. |

FOREIGN PATENT DOCUMENTS

| | | | |
|---|---|---|---|
| WO | 97/26847 A1 | 7/1997 | |
| WO | 99/02214 A1 | 1/1999 | |
| WO | 00/12033 A1 | 3/2000 | |
| WO | 00/74605 A1 | 12/2000 | |
| WO | 02/17825 A2 | 3/2002 | |
| WO | 03/002021 A2 | 1/2003 | |
| WO | 03/005937 A1 | 1/2003 | |
| WO | WO 2009032353 A1 * | 3/2009 | ......... A61B 17/3403 |

OTHER PUBLICATIONS

[No Author Listed] chronOS Perfusion Concept Technique Guide, Synthes, May 2010, pp. 1-32.

[No Author Listed] FDA Approves Cambridge Scientific, Inc.'s Orthopedic WISORB (TM) Malleolar Screw [online], Jul. 30, 2002, 5 pages. Retrieved from the Internet <URL: http://www.cambridgescientificinc.com/interbody.htm>, [retrieved on Oct. 14, 2003].

(56) References Cited

OTHER PUBLICATIONS

[No Author Listed] Longer BAK/L Sterile Interbody Fusion Devices. Date believed to be 1997. Product Data Sheet. Zimmer. Retrieved Jul. 23, 2012 from <http://catalog.zimmer.com/content/zpc/products/600/600/620/S20/S045.html>. 2 pages.

[No Author Listed] Osteoset® DBM Pellets (Important Medical Information) [online], Nov. 2002, 5 pages. Retrieved from the Internet <URL: http://www.wmt.com/Literature>, [retrieved on Oct. 14, 2003].

[No Author Listed] Percutaneous Autolgous Bone-marrow Grafting for Open Tibial Shaft Fracture (IMOCA) Aug. 6, 2007, ClinicalTrials. gov., 5 pages, last updated Aug. 29, 2011.

[No Author Listed] Plivios and Plivios chronOS Technique Guide, Synthes, Feb. 2011, pp. 1-36.

[No Author Listed] Sonic Accelerated Fracture Healing System/Exogen 3000. Premarket Approval, U.S. Food & Drug Administration. Date believed to be May 10, 2000, 4 pages. Retrieved Jul. 23, 2012 from <http://www.accessdata.fda.gov/scripts/cdrh/cfdocs/cfPMA/pma.cfm?id=14736#>.

Barakat et al., 1996.

Becker, S., et al., Osteopromotion by a beta-tricalcium phosphate/bone marrow hybrid implant for use in spine surgery. Spine (Phila Pa 1976). Jan. 1, 2006;31(1):11-7.

Bhargava, "Percutaneous autologous bone marrow injection in the treatment of delayed or nonunion", Indian J Orthop, Jan.-Mar. 2007, vol. 41(1 ), pp. 67-71.

Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.

Bruder et al., Monoclonal antibodies reactive with human osteogenic cell surface antigens. Bone. Sep. 1997;21(3):225-235.

Burkoth et al., A review of photocrosslinked polyanhydrides: in situ forming degradable networks. Biomaterials. Dec. 2000;21(23):2395-2404.

Curylo, L.J., et al., Augmentation of spinal arthrodesis with autologous bone marrow in a rabbit posterolateral spine fusion model. Spine (Phila Pa 1976). Mar. 1, 1999;24(5):434-8; discussion 438-9.

Domb, 1996.

Flemming et al., Monoclonal anitbody against adult marrow-derived mesenchymal stem cells recognizes developing vasculature in embryonic human skin. Developmental Dynamics. 1998;212:119-132.

Gennaro, A.R., ed., Remington: The Science and Practice of Pharmacy. Williams & Wilkins, 19th edition, Jun. 1995.

Haas, Norbert P., New Products from AO Development [online], May 2002, 21 pages. Retrieved from the Internet <URL:http://www.ao.asif.ch/development/pdf_tk_news_02.pdf>, [retrieved on Oct. 14, 2003].

Hao et al., Investigation of nanocomposites based on semi-interpenetrating network of [L-poly (epsilon-caprolactone)]/[net-poly(epsilon-caprolactone)] and hydroxyapatite nanocrystals. Biomaterials. Apr. 2003;24(9):1531-9.

Haynesworth et al., Cell surface antigens on human marrow-derived mesenchymal cells are detected by monoclonal antibodies. Bone. 1992;13(1):69-80.

Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.

Invitation to Pay Additional Fees dated Aug. 10, 2004 for Application No. PCT/US2004/004284 (8 Pages).

International Search Report and Written Opinion dated Oct. 29, 2004 for Application No. PCT/US2004/004284 (17 Pages).

International Preliminary Report on Patentability dated Feb. 15, 2005 for Application No. PCT/US2004/004284 (8 Pages).

Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).

Kricheldorf and Kreiser-Saunders, 1996.

Kroschwitz et al., eds., Hydrogels. Concise Encyclopedia of Polymer Science and Engineering. Wiley and Sons, pp. 458-459, 1990.

Lange, A.L., Lange's Handbook of Chemistry. McGraw-Hill Inc., 13th edition, Mar. 1985.

Lendlein et al., AB-polymer networks based on oligo(epsilon-caprolactone) segments showing shape-memory properties. Proc Natl Acad Sci U S A. Jan. 30, 2001;98(3):842-7. Epub Jan. 23, 2001.

Malberg, M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.

Massia and Hubbell, 1991.

McAfee et al., Minimally invasive anterior retroperitoneal approach to the lumbar spine: Emphasis on the lateral BAK. Spine. 1998;23(13):1476-84.

Mendez et al., Self-curing acrylic for+A43:A66mulations containing PMMA/PCL composites: properties and antibiotic release behavior. J Biomed Mater Res. Jul. 2002;61(1):66-74.

Neiman, "Treatment of Tibial Nonunion and Delayed Union by Percutaneous Injection of Concentrated Autologous Stem Cells: An Alternative to Open Surgical Repair—a Case Report", 2 pages, 2007.

New Zealand Office Action dated Jul. 9, 2007 for Application No. 541626 (3 Pages).

Pederson, A.W., et al., Thermal assembly of a biomimetic mineral/collagen composite. Biomaterials. Nov. 2003;24(26):4881-90.

Regan et al., Endoscopic thoracic fusion cage. Atlas of Endoscopic Spine Surgery. Quality Medical Publishing, Inc. 1995;350-354.

Sebecić, B., et al., Percutaneous autologous bone marrow grafting on the site of tibial delayed union. Croat Med J. Sep. 1999;40(3):429-32.

Slivka et al., In vitro compression testing of fiber-reinforced, bioabsorbable, porous implants. Synthetic Bioabsorbable Polymers for Implants. STP1396, pp. 124-135, ATSM International, Jul. 2000.

Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

Timmer et al., In vitro degradation of polymeric networks of poly(propylene fumarate) and the crosslinking macromer poly(propylene fumarate)-diacrylate. Biomaterials. Feb. 2003;24(4):571-7.

United States Disctrict Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.

Walsh et al., Preparation of porous composite implant materials by in situ polymerization of porous apatite containing epsilon-caprolactone or methyl methacrylate. Biomaterials. Jun. 2001;22(11):1205-12.

\* cited by examiner

ASPIRATING IMPLANTS AND METHOD OF BONY REGENERATION

CROSS-REFERENCE TO RELATED APPLICATIONS

This application is a continuation of U.S. patent application Ser. No. 15/218,210 filed on Jul. 25, 2016, which is a continuation of U.S. patent application Ser. No. 14/877,901 filed on Oct. 7, 2015 (now abandoned), which is a continuation of U.S. patent application Ser. No. 12/634,647 filed on Dec. 9, 2009 (now U.S. Pat. No. 9,168,138), each of which is hereby incorporated herein by reference in its entirety.

BACKGROUND OF THE INVENTION

Because bone regeneration is generally required to obtain successful outcomes for many common orthopedic procedures, osteoregenerative products such as allograft, bone substitutes, morphogenic proteins and osteoregenerative mixes are widely used by clinicians. In these procedures, both compression-resistant and non-compression resistant bone substitutes are frequently mixed with allograft as well as autologous materials including marrow and bone.

Current procedures for harvesting autologous stem cells from bone marrow have incorporated methods to enhance stem cell filtering, mixing or seeding to improve viability of implant matrixes. For example, U.S. Pat. No. 5,824,084 (Muschler) discloses a method of preparing a composite bone graft. Unfortunately, some disadvantages are associated with these procedures. For example, the time and exposure required during the mixing of bone, bone substitutes matrix's with autologous bone or aspirate can significantly delay the surgical procedures, increasing the risk of infection and blood loss.

Also, the bone marrow aspiration procedure often requires an added surgery for harvesting of BMA or bone from adjacent vertebrae, processes, ribs or the iliac crest. Spinal surgical fusion procedures require the endplates to burred and roughened to allow marrow to bleed into the interbody graft. This added time and effort increases operating room demand, anesthesia requirements, infectious disease exposure, and blood loss, all of which impact patient outcomes as well as procedure cost. Lastly, conventional prefilled graft materials are not designed to maximize stem cell retention.

Thus, there is a need for a procedure and devices for harvesting stem cells that reduces collateral damage, infection risk, operating room time, operating room effort for graft mixing and packing, and provides a graft that enhances stem cell attachment.

US Published Patent Application No. 2008154377 (Voellmicke) discloses an intervertebral fusion cage that is adapted to contain an inserter within its inner volume during insertion of the cage.

Curylo, Spine, 24(5), 1 Mar. 1999, pp 434-438 discloses augmentation of spinal arthrodesis with autologous bone marrow in a rabbit posterolateral spine fusion model.

Božidar Šebečiæ, Croatian Medical Journal, March 1999 (Volume 40, Number 3) discloses percutaneous autologous bone marrow grafting on the site of tibial delayed union.

Becker, Spine, 31 (1), 2006, pp. 11-17, discloses osteopromotion by a β-tricalciutn phosphate/bone marrow hybrid implant for use in spine surgery.

SUMMARY OF THE INVENTION

This invention provides devices and methods for the in-situ drawing, filtering and seeding of cells from the marrow of surrounding bone into an implanted fusion cage.

In particular, the present invention includes various implants with aspiration ports and other devices that enable in-situ harvesting and mixing of stem cells. These devices may include spinal fusion cages, long bone spacers, lateral grafts and joint replacement devices. Each implant utilizes at least one aspiration port for the in situ harvesting of stem cell-containing marrow via aspiration from adjacent decorticated bony elements.

In some embodiments, some of the following components that enable stem cell collection are employed:
  fusion device aspiration ports,
  fusion device covers or sheaths that improve the suction through the cage;
  porous sheets that allow suction therethrough but retain cells,
  graft matrixes designed for controlled stem cell filtering, collection and bony regeneration, and
  insertion and aspiration instruments including a flexible aspiration funnel.

These components allow for effective retention of stem cells but without the time-consuming and invasive ex vivo harvesting, ex vivo mixing and ex vivo handling of conventionally-obtained graft.

Therefore, in accordance with the present invention, there is provided an intervertebral fusion assembly, comprising:
  a) an intervertebral fusion cage, comprising:
    i) an upper surface adapted for gripping an upper vertebral body and comprising an upper throughole therethrough,
    ii) a lower surface adapted for gripping a lower vertebral body and comprising a lower throughole therethrough,
    iii) a sidewall connecting the upper and lower surfaces and comprising an aspiration port therethrough, and
  b) an aspirator,
wherein the aspirator connects to the aspiration port to provide fluid connection between the fusion cage and the aspirator.

DETAILED DESCRIPTION OF THE INVENTION

Several aspirating devices and methods are disclosed that improve stem cell filtering, enhance mixing, increase bony regeneration, and reduce the risk of infection. These devices and methods include both implants and instruments that facilitate the in-situ aspiration and mixing of native autograft. The use of such devices and methods subsequently result in bone regeneration without the added operative procedure, manual variability and infection risk associated with the conventional harvesting and external mixing of stem cells.

In some embodiments, the aspiration port may be selected from the group consisting of a simple hole, a threaded hole, a pierceable membrane such as a septum, a cannulated projection extending out of the implant, and a recess extending into the implant. In some embodiments, the implant includes more than one such aspiration port.

The port (or aspiration line) may incorporate a one-way valve to enable aspiration while preventing subsequent leakage. The port (or aspiration line) may also have a bi-directional valve that enables both a) the aspiration of aspirate into the implant (by drawing a vacuum through the port), and b) the injection of biologics (such as cells, BMPs, drugs, anesthetics, analgesics, or antibiotics) directly into the porous matrix of the implant to enhance bone growth (by injecting through the port).

The ports may further include modular attachment means for intra-operative insertion, aspiration and/or injection.

The port may be designed to have a control feature that controls process variables such as flow rate, pressure and/or delivery of the aspirate through the porous bone substitute matrixes.

The implants may be in the form of a bag, tube or cage. They may be pre-operatively or intra-operatively filled with bone-inducing porous matrixes.

In the case of spinal fusion cages, openings in the bone-contacting surfaces (or endplates) of the cage enable marrow aspiration therethrough following aggravation of the natural endplates to initiate vascular/marrow flow. Such a cage having teeth on its endplates can be manipulated in-situ to decorticate the bone and thereby enhance vascular flow and aspirate filtering. The spinal-fusion cage can have limited lateral/posterior holes to control vacuum pressure and maximize vascular flow. The endplates of the cage may include peripheral sealing as a means to enhance flow, fit, or conformation or provide for added vacuum capabilities with adjacent endplates. The cage can be fabricated with or placed within a bag (made of, for example, collagen or resorbable polymer) to contain vascularity and stem cells during and after aspiration.

Figure 1A:
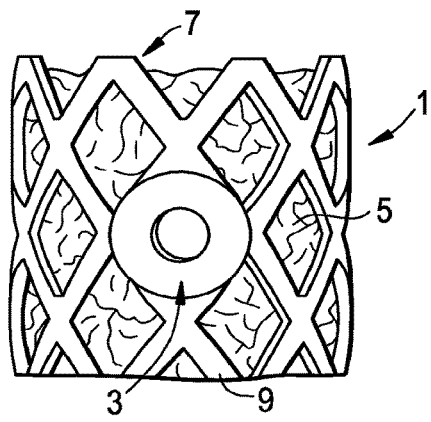
FIGS. 1A-1D disclose side and front views of intervertebral fusion cages of the present invention.
Figure 1B:
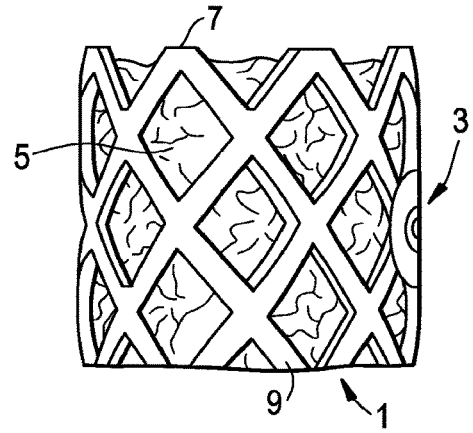
Figure 1C:
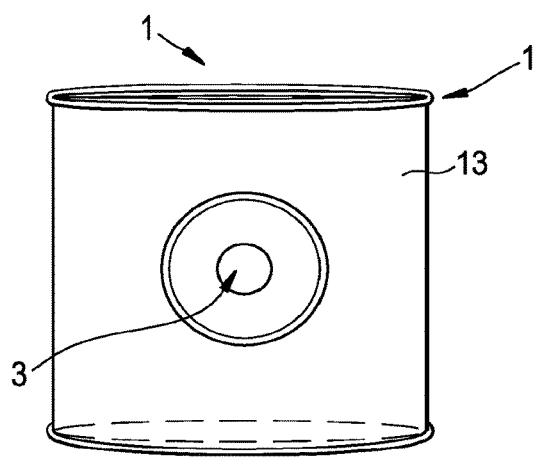
Figure 1D:
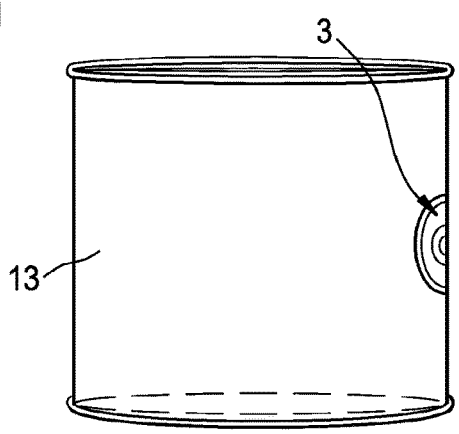

Now referring to FIGS. 1a-d, there are provided front and side views of intervertebral fusion cages of the present invention. FIGS. 1a-b disclose a standard mesh-type cage 1 fitted with an aspiration port 3. The cage has been filled with a porous matrix 5 (in this case, a bony regeneration matrix) to assist in the retention of the stem cells in the cage. In some embodiments, the upper 7 and lower 9 surfaces of the cage have been beveled to increase endplate vascularity. FIGS. 1c-d disclose front and side views of the cages of FIGS. 1a-b, but with a sheath 13 wrapped around the cylindrical portion of the cage. These sheaths helped retain the suction produced by the aspiration.

Figure 2A:
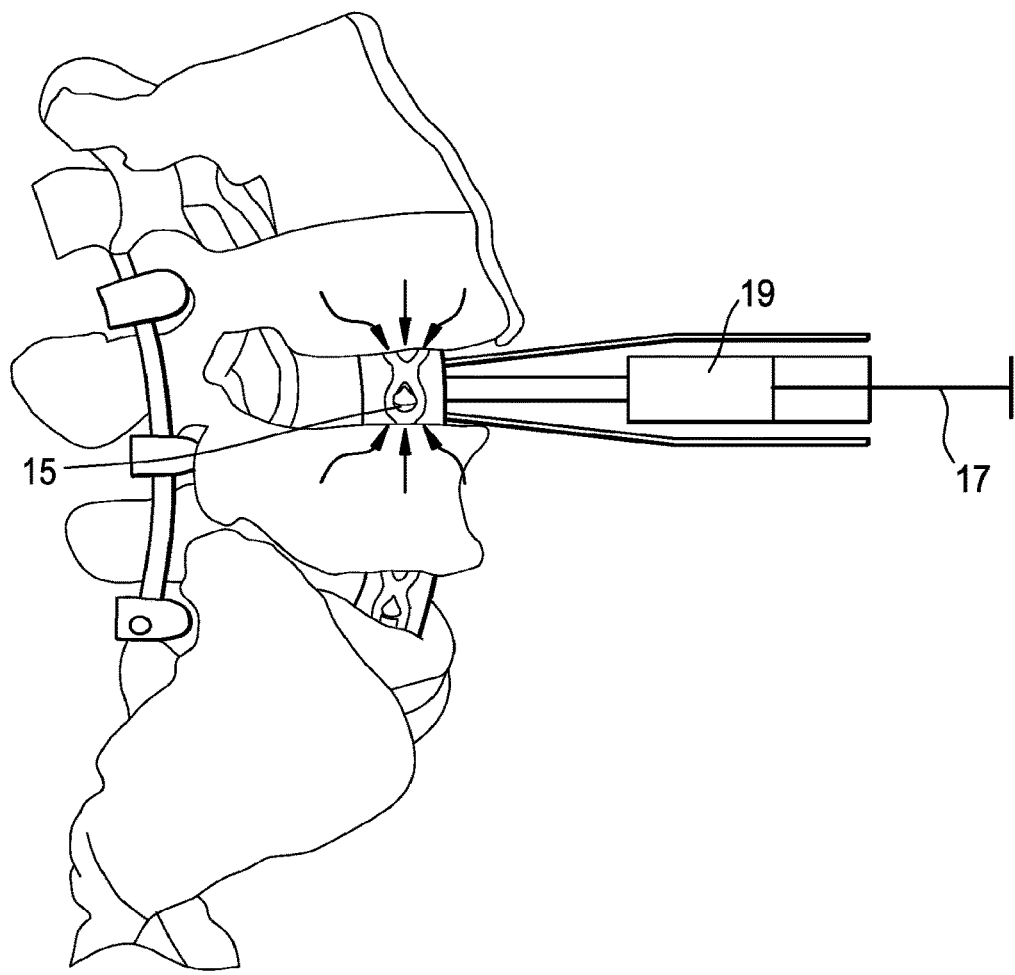
FIG. 2A discloses a side view of an assembly of the present invention, with the cage thereof implanted in a disc space.

Now referring to FIG. 2a, there is disclosed a side view of an assembly of the present invention, with the cage 15 thereof implanted in a disc space. In use, the plunger 17 of the aspiration syringe 19 is slowly withdrawn, thereby reducing the pressure in the air-tight cage. The low pressure in the cage causes bone marrow to move from the adjacent vertebral bodies into the cage (as shown by the plurality of arrows). The porous matrix provided in the cage retains the stems cells present in the marrow.

In some embodiments, the marrow collected in the syringe is re-injected through the cage in order to retain even more stem cells on the porous matrix.

Figure 2B:
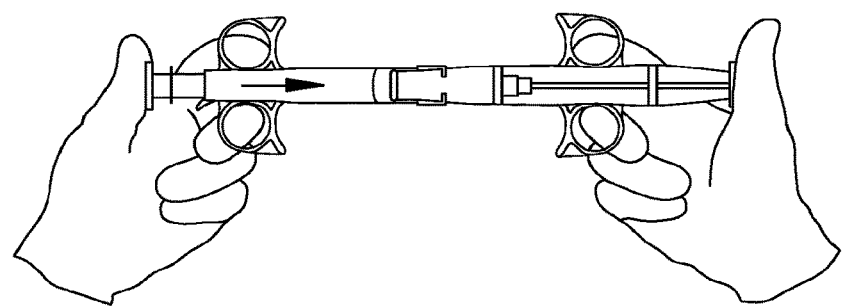
FIG. 2B discloses use of the assembly.

FIG. 2b discloses use of the assembly.

Figure 3A:
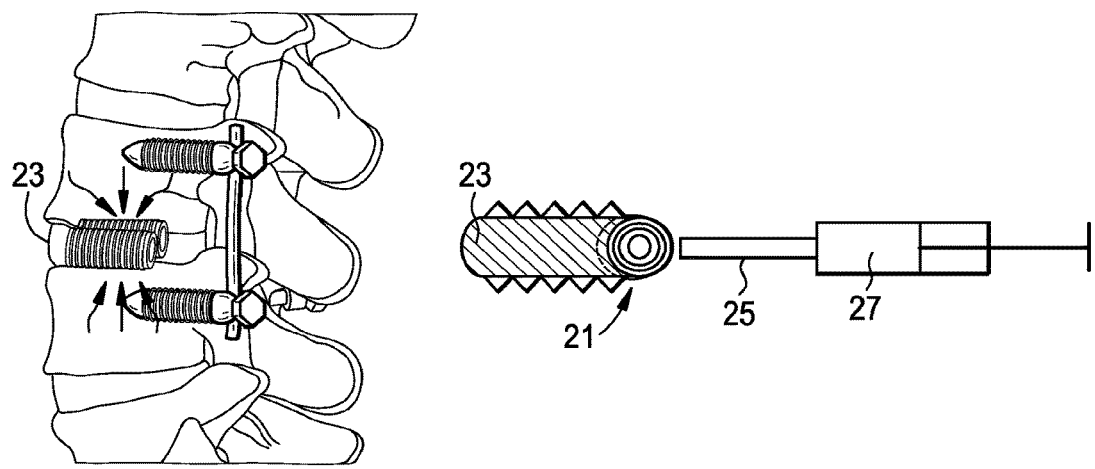
FIG. 3A discloses an exploded assembly of the present invention.
Figure 3B:
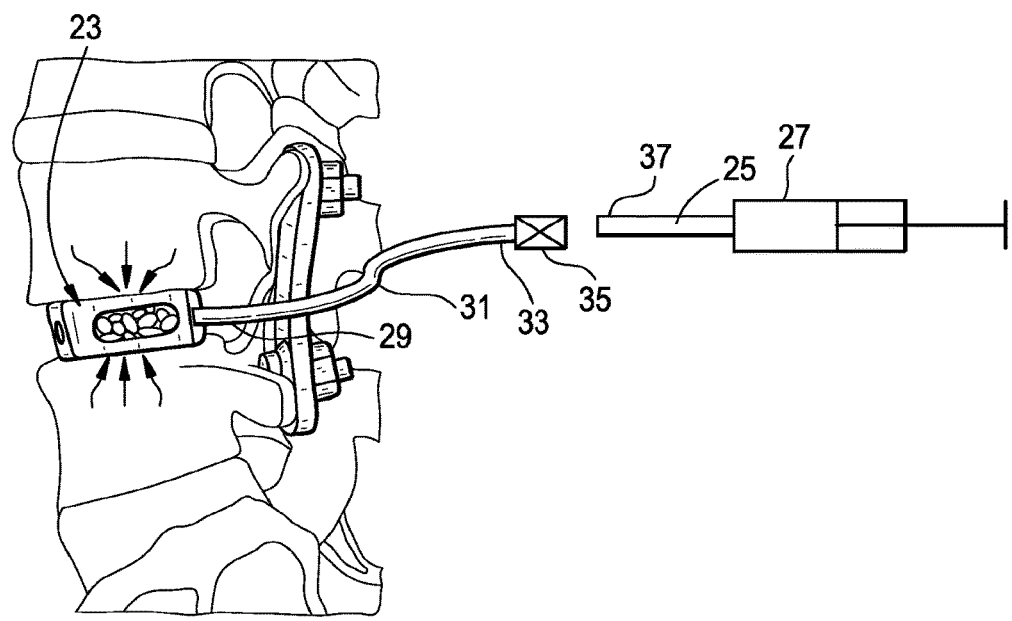
FIG. 3B discloses a side view of another exploded assembly of the present invention, with the cage thereof implanted in a disc space.

Now referring to FIGS. 3a-d, there are provided various aspirator cages of the present invention. FIG. 3a discloses an exploded assembly of the present invention in which the port 21 of the cage 23 is aligned with the needle 25 of an aspirating syringe 27. In FIG. 3b, there is a side view of another exploded assembly of the present invention, with the cage 23 thereof implanted in a disc space. The distal end 29 of an aspiration line 31 is connected to the port 21 of the cage 23, while the proximal end 33 of the line is fitted with a valve 35. The purpose of the valve is to allow for disconnection without leakage. During aspiration, the valve will hold the negative pressure. During dispensing, the valve insures the dispensing pressure and prevents leakage. The valve can also control excess vacuum pressure for a predetermined time.

Figure 3C:
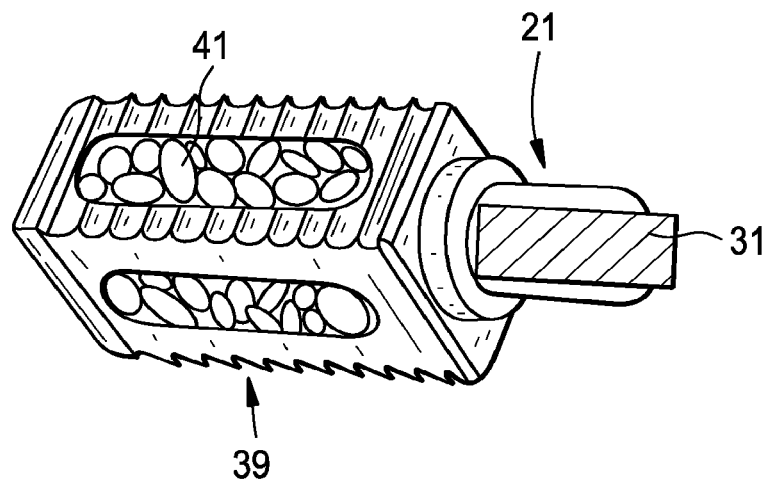
FIG. 3C discloses a perspective view of an aspiration cage of the present invention.
Figure 3D:
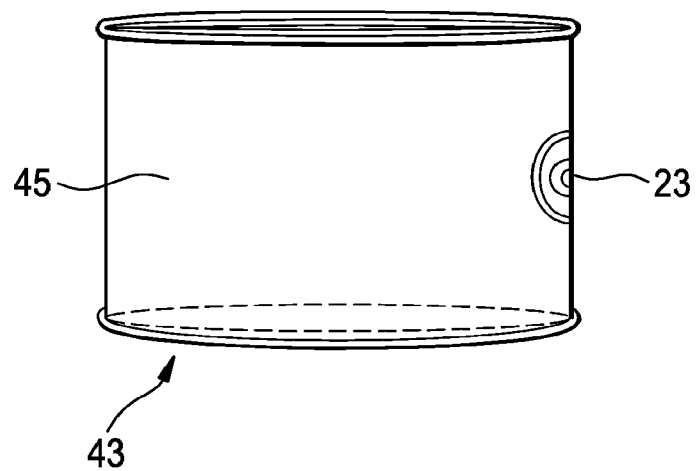
FIG. 3D discloses a side view of an aspiration cage of the present invention wrapped in a graft containment bag (or sheath).

The valve is also adapted for connection to the distal end 37 of the needle of an aspirating syringe 27. FIG. 3c discloses a perspective view of an aspiration cage 39 of the present invention. This cage has a port 21 to which an aspiration line 31 is connected. The cage is also filled with porous matrix 41 for retaining the stem cells thereon. FIG. 3d discloses a side view of an aspiration cage 43 of the present invention wrapped in a graft containment bag 45 (or sheath).

The aspirating and filtering devices of the present invention can also be used to create long bone graft spacers with enhanced viability and reduced surgical risk. These tubular spacers may be fabricated from polymers, ceramics, or bone substitutes. They can be preoperatively or intra-operatively filled with porous bone substitute matrixes. Aspiration port(s) on the long bone spacer enable marrow aspiration and stem cell filtering to enhance viability of the device.

Figure 4A:
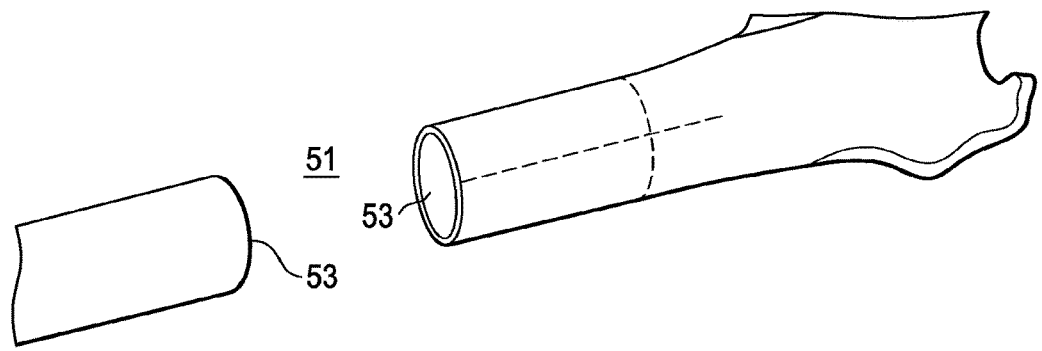
FIGS. 4A-4B disclose a tube-like load bearing device of the present invention implanted in a long bone.
Figure 4B:
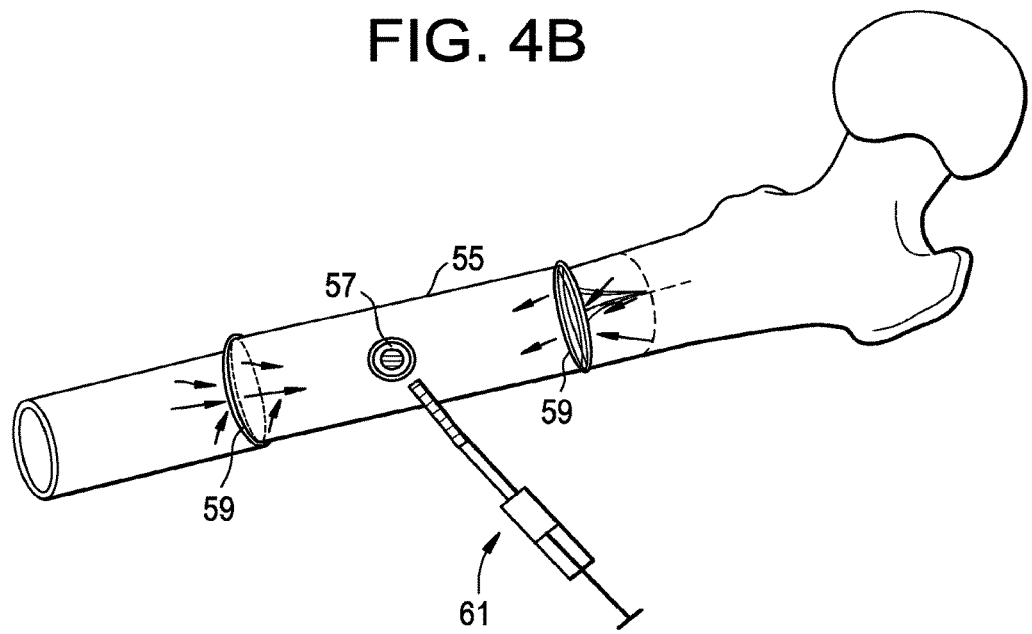

Therefore, and now referring to FIGS. 4a-b, there is provided a method of treating a long bone defect 51 having opposing cancellous surfaces 53, comprising the step of:
  a) inserting a fusion cage 55 into the defect, the cage having an aspiration port 57 and opposing porous endplates 59, b) orienting the cage so that each porous endplate of the cage abuts one of the cancellous surfaces,
c) fluidly connecting an aspirator 61 to the port, and
d) actuating the aspirator to lower pressure in the cage, thereby drawing bone marrow from the cancellous surfaces into the cage.

In one preferred embodiment, an implant of the present invention is used to improve the healing of a contained defect. In use, the defect is first is filled with bone substitutes or matrixes and covered with an osteoconductive porous sheet or matrix. In-situ bone marrow (containing stem cells) is then aspirated though the porous sheet and the stem cells are seeded onto the matrix and sheet. This procedure may be accomplished with or without an aspiration port via a flexible and conforming funnel aspirator. The funnel can be deployed minimally invasively to both deliver and implant the porous sheet onto the defect.

Figure 5A:
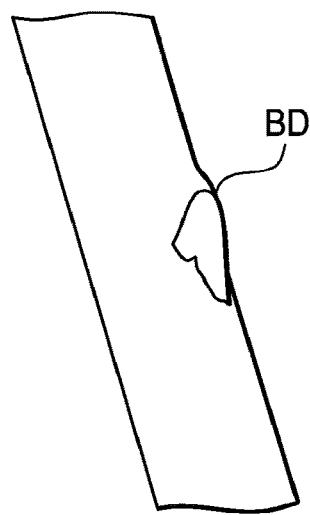
FIGS. 5A-5F disclose a method of the present invention being carried out in a long bone defect.
Figure 5B:
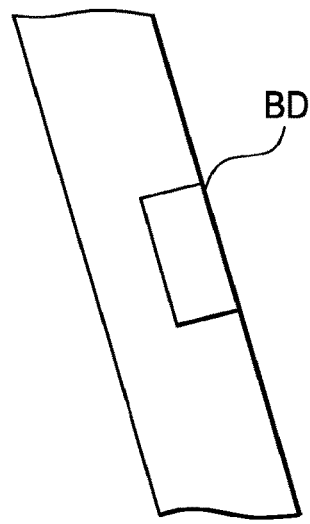
Figure 5C:
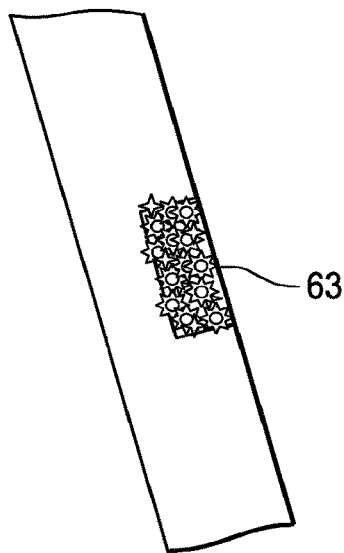
Figure 5D:
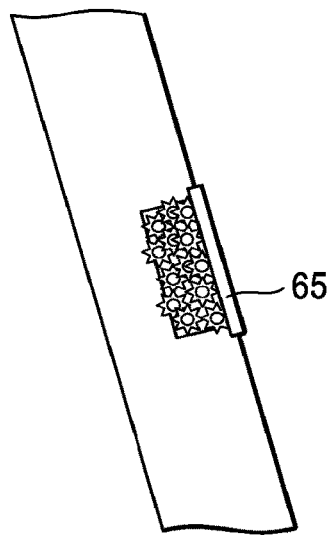
Figure 5E:
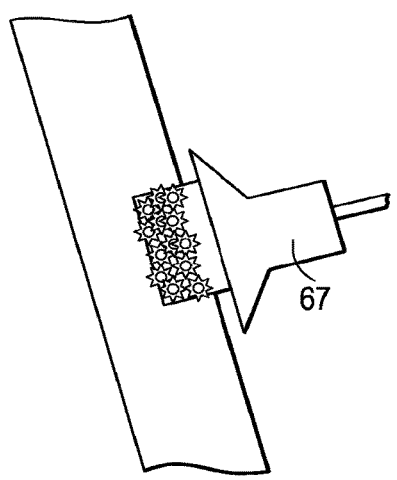
Figure 5F:
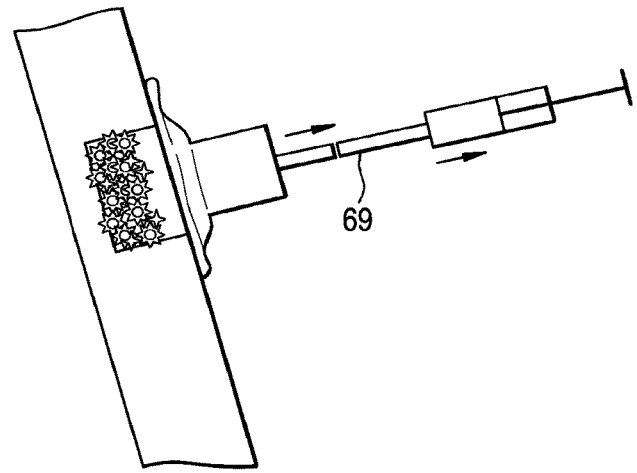

Now referring to FIG. 5a, the procedure begins with creating an approach to the bony defect BD. Now referring to FIG. 5b, the defect BD is debrided. Now referring to FIG. 5c, the debrided area is filled with a porous matrix 63 (for example, a bone substitute or an expandable gel). Now referring to FIG. 5d, a porous cover sheet 65 is applied over the porous matrix housed in the debrided area. The cover sheet is then attached with either fasteners or an adhesive (neither shown). Now referring to FIG. 5e, a flexible aspiration funnel 67 is then laid upon the porous cover sheet. Now referring to FIG. 5f, an aspirator 69 is fluidly connected to the funnel, and a vacuum is drawn through the cover sheet to aspirate marrow into the porous matrix. The vacuum pressure associated with the aspiration is monitored and cut off when a desired pressure is obtained, or when the cover sheet or matrix becomes occluded with marrow.

Therefore, in accordance with the present invention, there is provided a method of treating a contained bony defect, comprising the steps of:
a) debriding the bony defect,
b) filling the defect with a porous matrix,
c) placing a porous sheet over the porous matrix,
d) placing a flexible funnel on the porous sheet, the funnel being fluidly connected to an aspirator, and
e) actuating the aspirator to draw bone marrow from the defect into the porous matrix and cover sheet.

Figure 6:
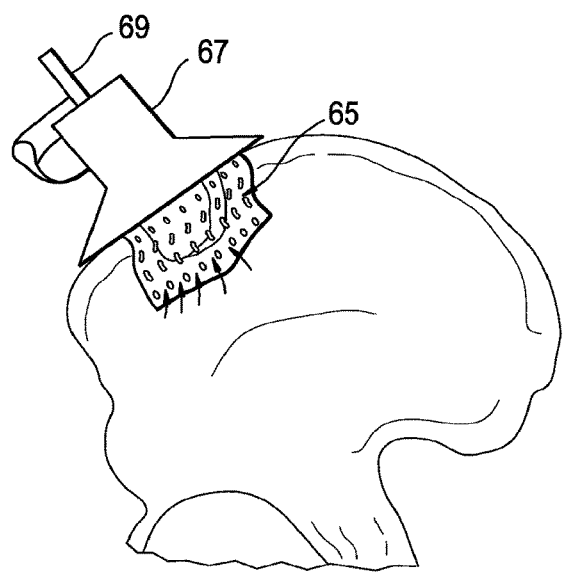
FIG. 6 discloses a method of the present invention being carried out on an iliac crest.

Now referring to FIG. 6, this flexible aspiration method described in FIGS. 5a-5f can also be utilized for other bony defects, including the iliac crest. Now referring to FIG. 6, there is provided a method of the present invention being carried out on an iliac crest, wherein the flexible funnel 67 and aspirator 69 draw bone marrow out of the pelvic region and into the porous matrix contained within the iliac crest so that the stem cells in the marrow are retained on the porous matrix.

Figure 7A:
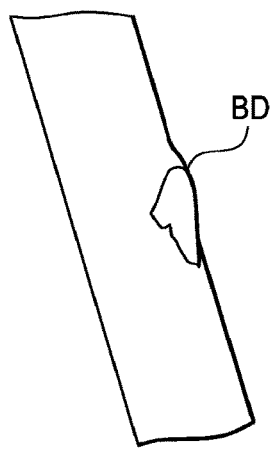
FIGS. 7A-7F disclose steps for implanting a long bone plug of the present invention in a contained bony defect.
Figure 7B:
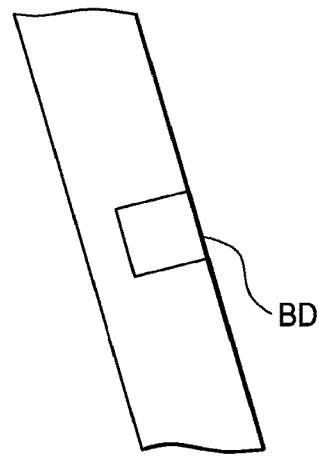
Figure 7C:
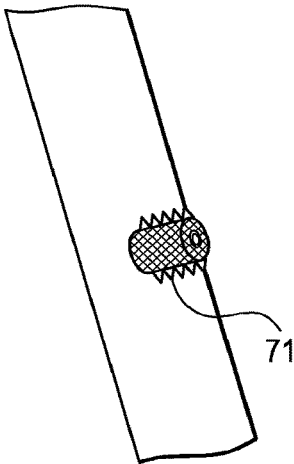

Now referring to FIGS. 7a-f, contained defects can be filled with aspirating bone plugs 71 that include ports or covers to facilitate marrow aspiration and stem cell filtering. FIG. 7a discloses such a preferred device of the present invention.

Figure 7D:
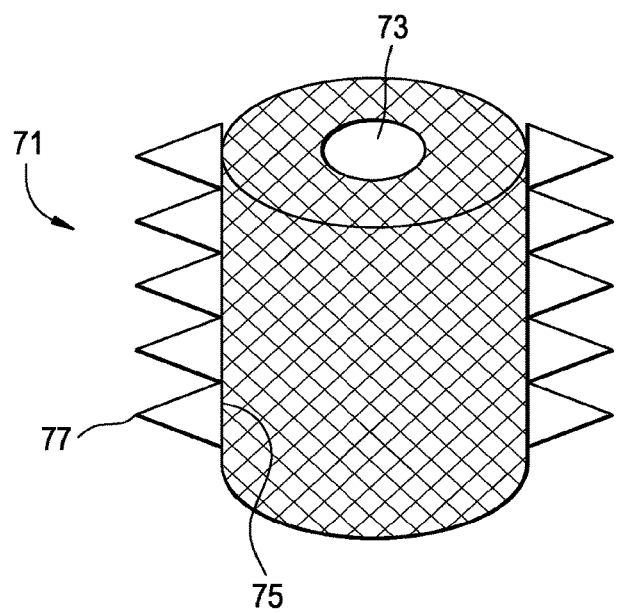
Figure 7E:
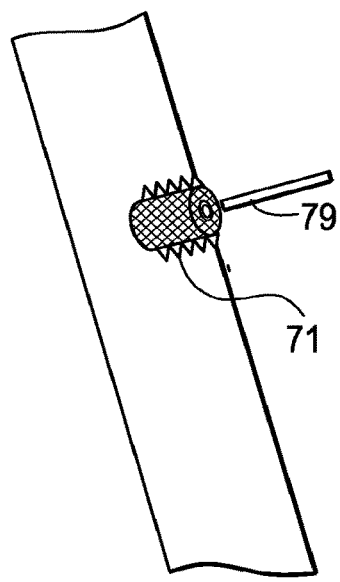
Figure 7F:
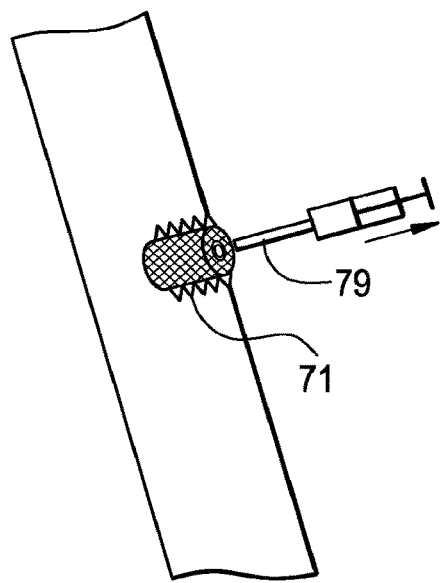

Now referring to FIG. 7a, the procedure begins with creating an approach to the bony defect BD. Now referring to FIG. 7b, the defect BD is debrided. Now referring to FIG. 7c, the debrided area is filled with a fusion device 71 consisting essentially of inorganic bone or bone substitute. FIG. 7d shows a side view of the fusion device of FIG. 7c. This allograft device is cylindrical in structure and made from a portion of a human femoral, tibial or ulnar long bone. On one end of the device, there is an aspiration port 73 adapted for connection to an aspirator. On the peripheral surface 75 of the device, there are a plurality of securement features 77 (such as teeth). In some embodiments, the device is fabricated from bone substitute and made so that its pores facilitate growth in the longitudinal/axial direction. Now referring to FIG. 7e, an aspirator (such as a syringe 79) is fluidly connected to the port of the fusion device. Lastly, and now referring to FIG. 7f, aspiration is applied to draw marrow out of the adjacent bone and into the porous bone plug, wherein the stem cells are retained.

Therefore, in accordance with the present invention, there is provided a method of treating a contained bony defect, comprising the steps of:
a) debriding the bony defect,
b) filling the defect with a porous allograft plug,
c) fluidly connecting the plug to an aspirator, and
d) actuating the aspirator to draw bone marrow from the defect into the porous allograft plug.

In some embodiments, the bone substitutes can be in the form of prefabricated semi-porous bags that are placed within bony structures to enable aspiration of stem cell from adjacent bony structures. The "graft jacket" may be utilized for lateral graft in spinal procedures. This device is placed in a generally axial direction to provide intimate contact against opposing transverse processes, which can be intraoperatively burred to enhance vascularity.

Figure 8:
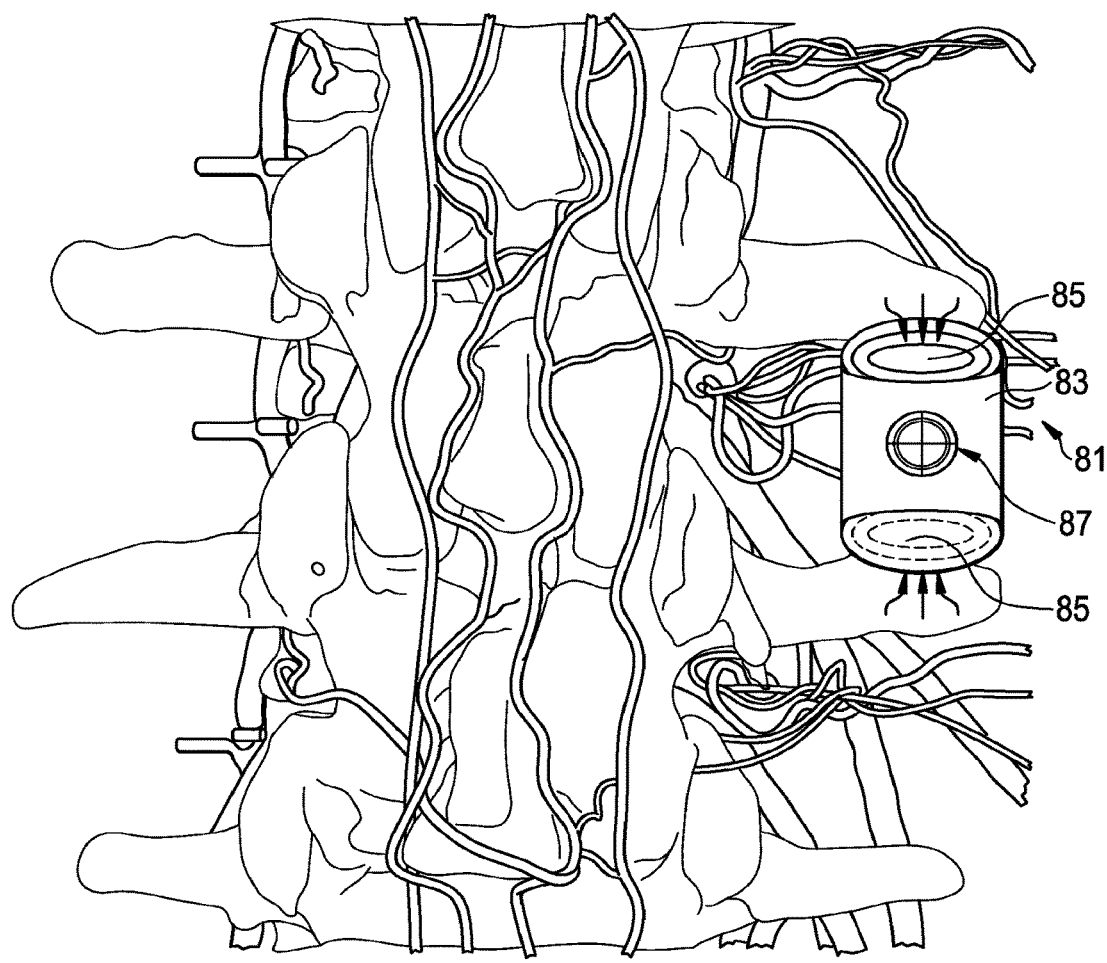
FIG. 8 discloses an aspirating graft jacket implanted between adjacent transverse processes.

Now referring to FIG. 8, there is provided an aspirating graft jacket of the present invention. The graft jacket 81 comprising:
a) an expandable bag 83 having upper and lower throughholes 85 and an aspiration port 87, and
b) a porous matrix (not shown) contained within the bag.

In use, the surgeon first aggravates the opposing faces of adjacent transverse processes in order to induce blood flow. Next, the surgeon places the aspirating graft jacket between the transverse processes, with the throughholes contacting the aggravated faces of the transverse processes. Next, the surgeon places an aspirator in fluid connection with the aspiration port of the graft jacket. Lastly, the surgeon applies a vacuum to the aspirator to draw marrow from the transverse processes and into the graft jacket.

Therefore, in accordance with the present invention, there is provided a method of fusing a spine between adjacent transverse processes, comprising the steps of:
a) decorticating opposing faces of the adjacent transverse processes,
b) placing a graft jacket having an aspiration port between the opposing faces so that upper and lower throughholes of the graft jacket contact the opposing faces,
c) fluidly connecting the port to an aspirator, and
d) actuating the aspirator to draw bone marrow from the transverse processes into the cage.

Figure 9:
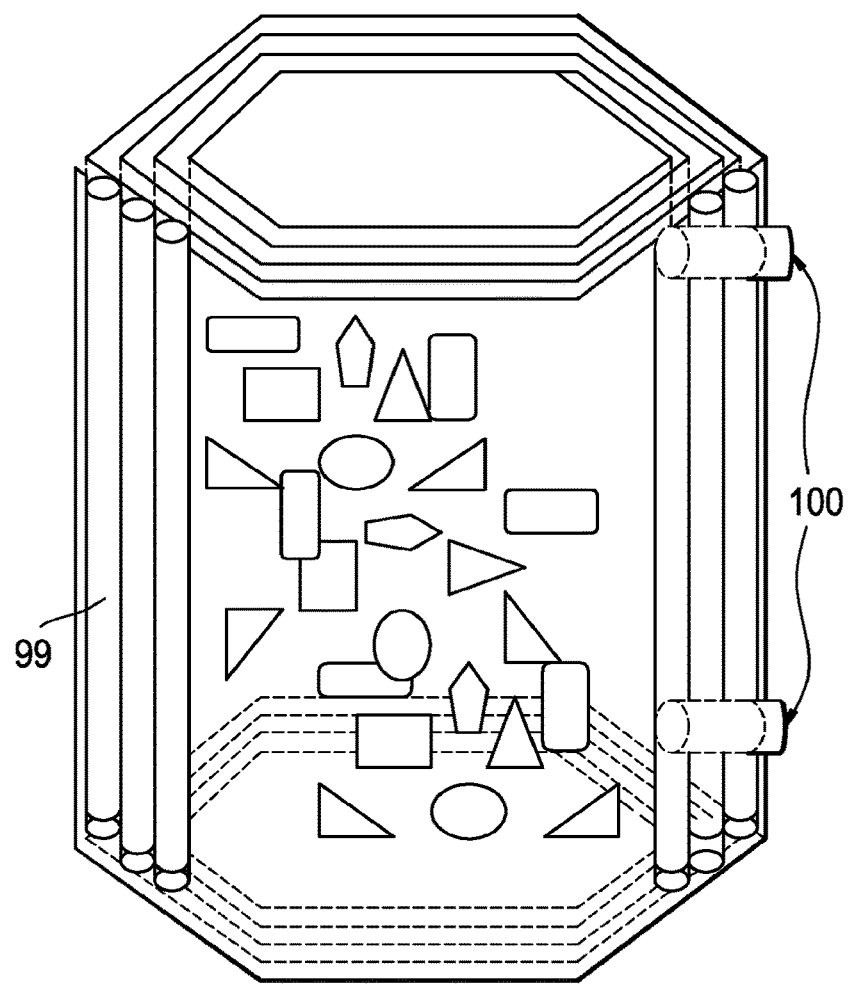
FIG. 9 discloses an aspirating graft jacket having nanotubes.

Now referring to FIG. 9, in some embodiments, the graft jacket of the present invention may contain nanotubes 99 extending longitudinally between the opposing open endfaces of the cage having ports 100. The axial nature of the nanotubes augments the load-bearing abilities of the graft jacket and further aids the capillary wicking of vascular flow to further enhance directional bone formation. Nanotubes can be produced from either carbon, metallics (titanium), polymers (such as PEEK, CFRP, or PET), or ceramics. Nanotubes can be produced from bone substitutes including CaP, HA, or TCP.

Figure 10A:
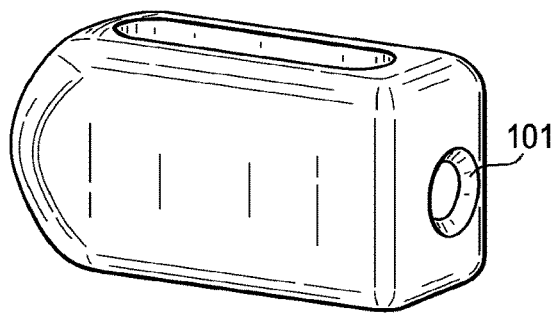
FIGS. 10A-10D disclose cages of the present invention with various ports.
Figure 10B:
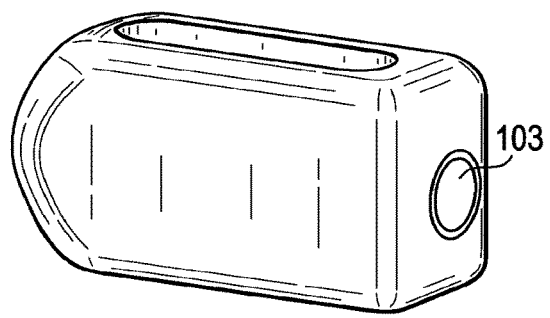
Figure 10C:
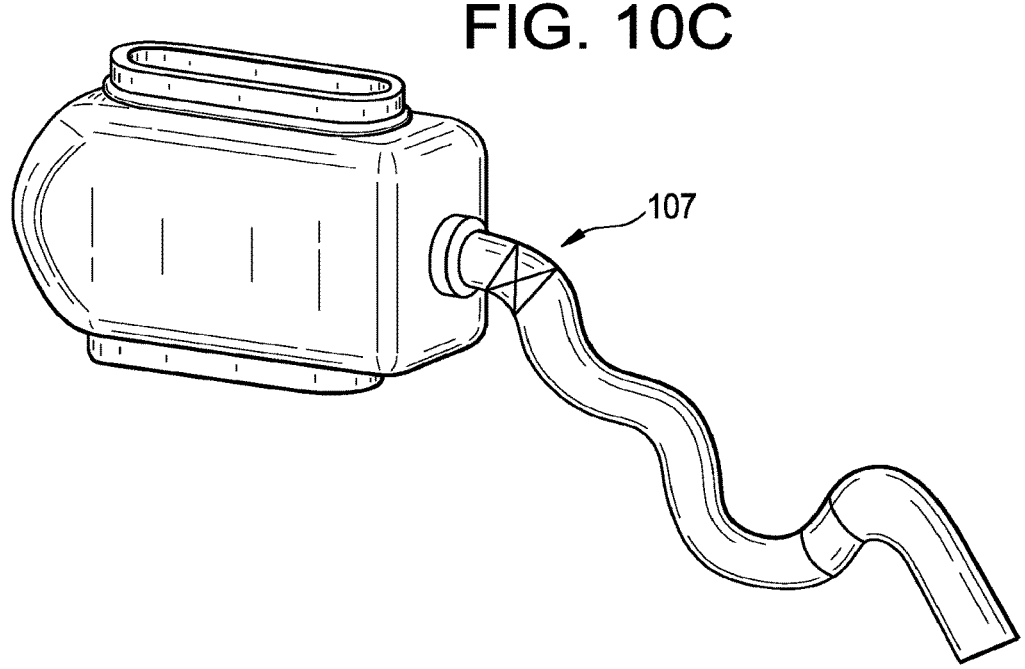
Figure 10D:
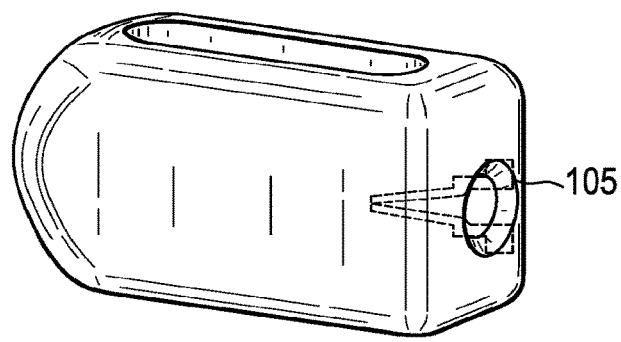
Figure 10E:
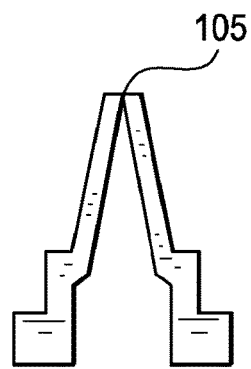
FIGS. 10E-10F disclose side and front views of a duckbill-type enclosed valve.
Figure 10F:
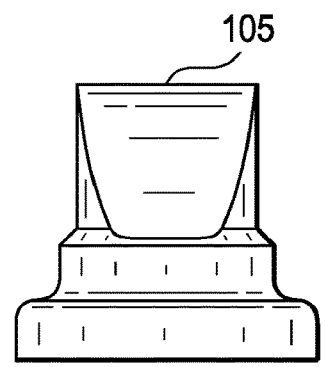

Now referring to FIGS. 10a-f, there are provided other embodiments of an intervertebral cage having a port. The port may be in the form of an opening 101 (as in FIG. 10a), a septum 103 (as in FIG. 10b), an enclosed valve 105 (as in FIG. 10d), or an in-line valve 107 (as in FIG. 10c). When an enclosed valve is selected, it is preferably in the form of a duckbill-type valve, as shown in FIGS. 10e and 10f. The port may be advantageously used for a) in-situ aspiration of autologous material (such as adjacent blood, marrow and stem cells); b) dispensing of bioreactive materials (such as graft, INJECTOS, bone marrow aspirate, and growth factors such as BMPs); and c) re-dispensing of materials post operatively (such as in the event of a failed fusion).

Figure 11:
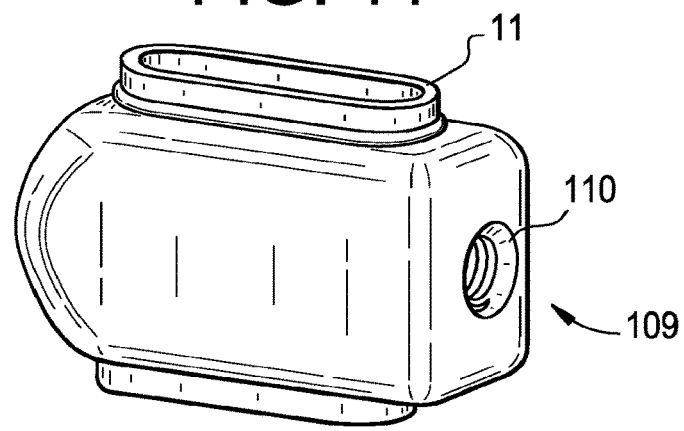
FIG. 11 discloses an aspirating cage of the present invention having an endplate seal.

Now referring to FIG. 11, there is provided another embodiment of the present invention describing a cage 109 with a port 110 and a compressible endplate seal 11. The compressible endplate seal typically lines an opening in the top or bottom of the cage and is made of elastomers (such as urethane, TPE, thermoplastic polymers and silicones), hydrogels, flexible resorbable polymers, or collagen. The compressible endplate seal provides a number of advantageous functions, including enhancing endplate contact, enhancing vacuum of adjacent marrow, containing aspirate, and containing dispensate.

Therefore, in accordance with the present invention, there is provided an intervertebral fusion cage, comprising:
 a) an upper surface adapted for gripping an upper vertebral body and comprising an upper throughole therethrough,
 b) a lower surface adapted for gripping a lower vertebral body and comprising a lower throughole therethrough,
 c) a sidewall connecting the upper and lower surfaces and comprising an aspiration port therethrough, and
at least one compressible endplate seal disposed about either the upper or lower throughhole.

Figure 12:
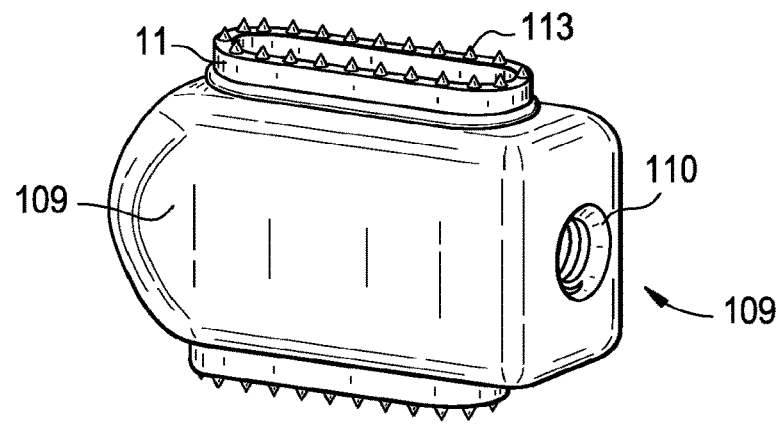
FIG. 12 discloses an aspirating cage of the present invention in which the endplate seal has teeth extending therefrom.

Now referring to FIG. 12, there is provided another embodiment of the present invention, describing a cage with a port, an endplate seal and a plurality of teeth 113 extending from the seal. The teeth may be used for gripping the opposing endplates and to initiate bleeding bone and marrow flow.

In some embodiments, the teeth that extend from the cage of the present invention are cannulated. These cannulated teeth can be deployed into the endplates once the cage is placed into the interbody space. In some embodiments, the inserter has a feature that triggers the spikes to deploy after insertion. Thus once the syringe is attached it would draw in marrow from the endplates through the holes in these cannulated teeth.

Figure 13:
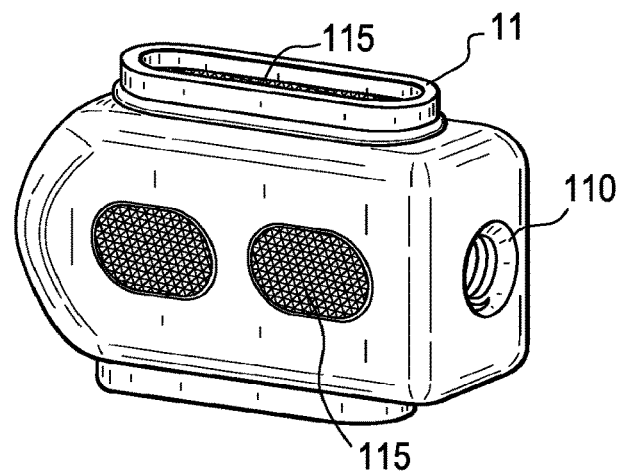
FIG. 13 shows an aspirating cage of the present invention filled with a porous matrix.

Now referring to FIG. 13, there is provided another embodiment of the present invention describing a cage with a port, an endplate seal with teeth, and a prefilled graft 115 within the cage. The graft acts as a filter to desirably increase stem cell selection/retention. In some embodiments, the graft has a pore size of between about 10 and about 20 μm and is treated with one or more of the following.
 a. Type 1 or 2 collagen,
 b. fibrinogen, fibronectin, and/or thrombin, or
 c. gelatin.

In some embodiments, a sheath (not shown) may be disposed around the cage of FIG. 13. The sheath may be used to advantageously enhance vacuum of adjacent marrow, contain aspirate, and contain dispensate.

Figure 14A:
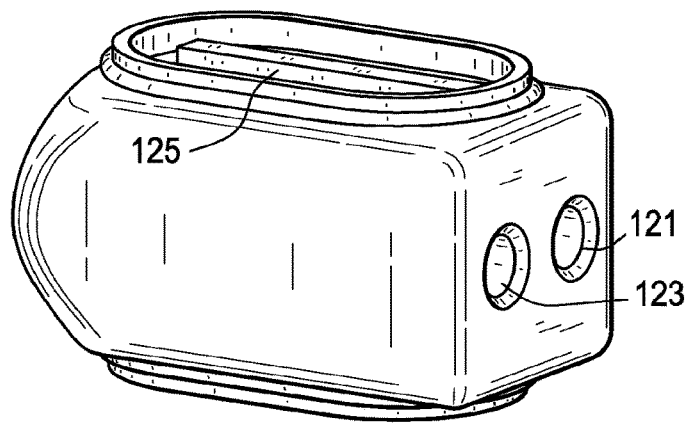
FIGS. 14A-14C show an aspirating cage of the present invention having two ports.
Figure 14B:
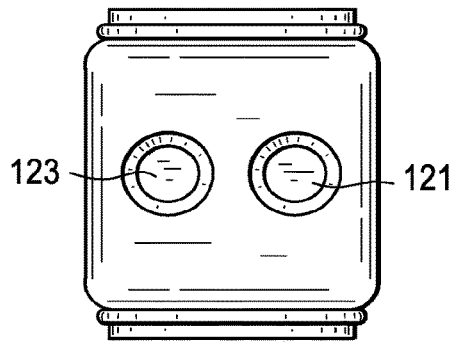
Figure 14C:
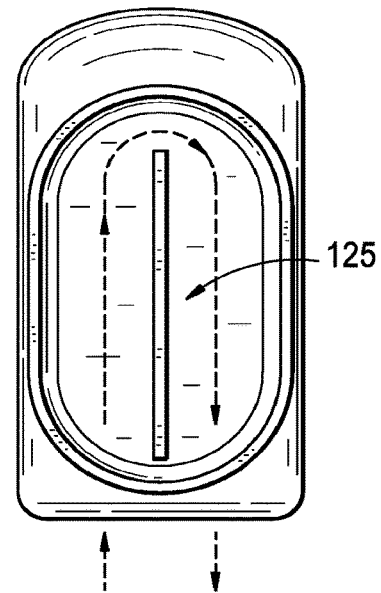

Now referring to FIG. 14, there is provided another embodiment of the present invention describing a cage having two ports 121, 123. The pair of ports can be used to provide for dual aspiration. One of the ports can be a dedicated dispensing port for dispensing materials such as bone marrow aspirate, PRP, growth factors such as BMP. The dual ports can be used with a baffle 125 to set up circulation in the cage (with one port allowing inflow and the other allowing only outflow, as in FIG. 14 c). In one such circulation embodiment, the circulation provides for enhanced filtering. In another embodiment, recirculation is provided.

Figure 15:
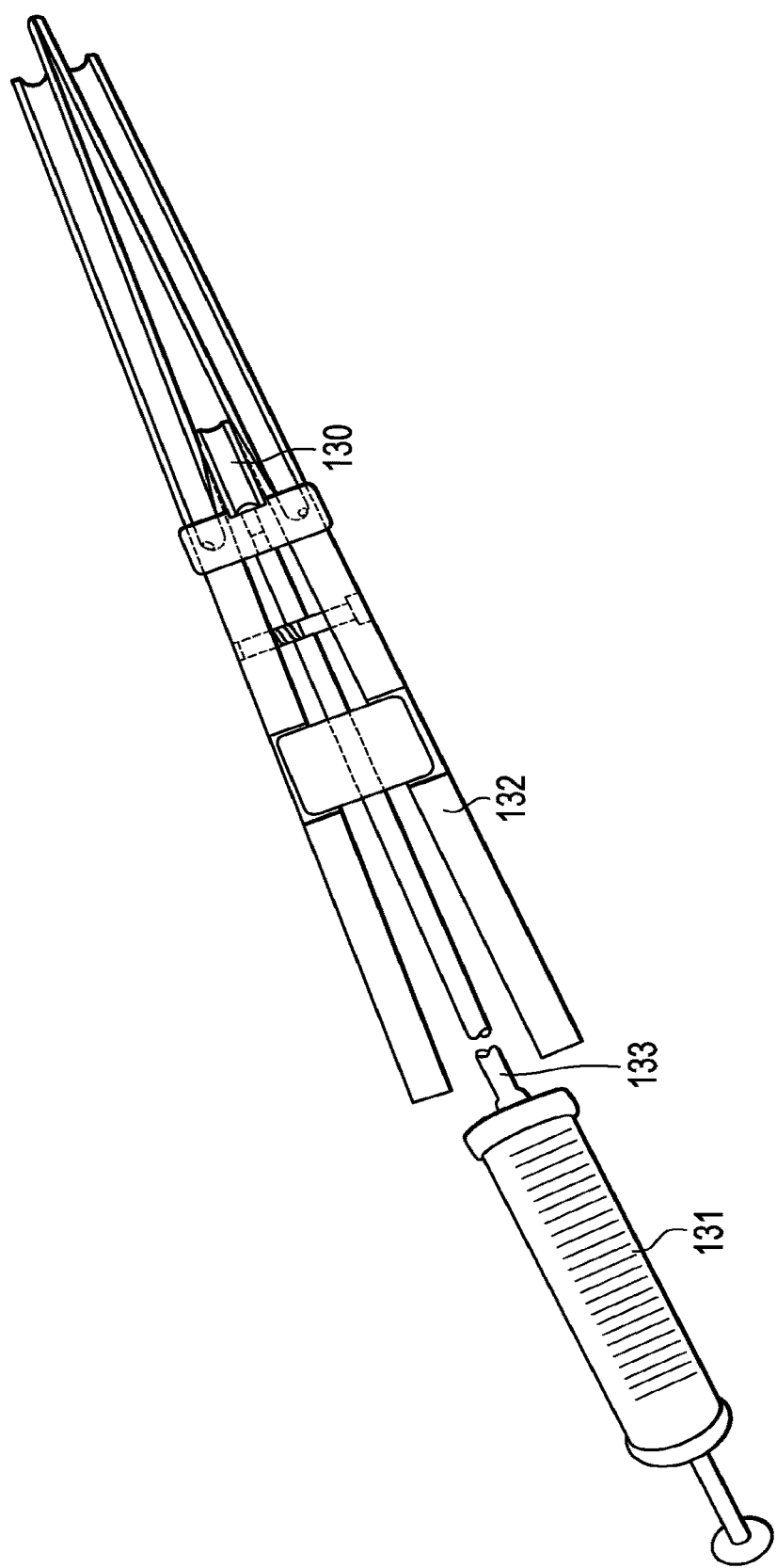
FIG. 15 discloses the cage of the present invention attached to an insertion device.

Now referring to FIG. 15, in some embodiments, the cage 130 may be inserted into the disc space with an inserter 132 substantially similar to that disclosed in U.S. Pat. Nos. 6,478,800 and 6,755,841 (the specifications of which are hereby incorporated by reference in their entireties), but with a syringe 131 and needle 133 replacing the medial shaft that connects with the implant.

In some embodiments, sufficient bone marrow is drawn into the cage to substantially fill the cage with bone marrow. However, it is known that stem cells selectively adhere to the surfaces of many porous media. Therefore, in other embodiments, an excess of bone marrow is drawn from the vertebral bodies and through the cage in order to concentrate the stem cells in the porous media of the cage.

The porous media is made from a biocompatible, implantable graft material. Preferably, the material has a charged surface. Examples of biocompatible, implantable graft materials having a charged surface include synthetic ceramics comprising calcium phosphate, some polymers, demineralized bone matrix, or mineralized bone matrix.

More preferably, cell adhesion molecules are bound to the surface of the porous media. The term "cell adhesion molecules" includes but is not limited to laminins, fibronectin, vitronectin, vascular cell adhesion molecules (V-CAM), intercellular adhesion molecules (I-CAM) and collagen.

In some embodiments, the cell adhesion molecule preferentially binds stem cells. In other embodiments, the cell adhesion molecule has a low affinity for partially or fully differentiated blood cells.

In some embodiments, the cage of the present invention includes a drug delivery reservoir. These reservoirs serve the same function as drug delivery microspheres but provide a more structured approach.

It is believed that a consistent and controlled flow rate of marrow through the cage will create the environment best suited for cell attachment. Preferably, the cage is designed (and the flow rate is selected) so that the flow of marrow therethrough fills the porous matrix in a reasonable time period, but does not flow so fast that shear stresses cause the stem cells to lyse.

The load-bearing fusion device of the present invention may be constructed of metals (such as Ti, Ti64, CoCr, and stainless steel), polymers (such as PEEK, polyethylene, polypropylene, and PET), resorbable polymers (such as PLA, PDA, PEO, PEG, PVA, and capralactides), and allograft, bone substitutes (such as TCP, HA, and CaP)

The fusion device housing of the present invention can be made of any structural biocompatible material including resorbable (PLA, PLGA, etc.), non-resorbable polymers (CFRP, PEEK, UHMWPE, PDS), metallics (SS, Ti-6Al-4V, CoCr, etc.), as well as materials that are designed to encourage bony regeneration (allograft, bone substitute-loaded polymers, growth factor-loaded polymers, ceramics, etc.). The materials for the fusion device housing are biocompatible and generally similar to those disclosed in the prior art. Examples of such materials are metal, PEEK and ceramic.

In preferred embodiments, the fusion device housing is manufactured from a material that possesses the desirable strength and stiffness characteristics for use as a fusion cage component. These components of the present invention may be made from any non-resorbable material appropriate for human surgical implantation, including but not limited to, surgically appropriate metals, and non-metallic materials, such as carbon fiber composites, polymers and ceramics.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany.

In some embodiments, the cage member comprises PEEK. In others, it is a ceramic.

In some embodiments, the fusion device housing consists essentially of a metallic material, preferably a titanium alloy or a chrome-cobalt alloy.

In some embodiments, the fusion device housing components are made of a stainless steel alloy, preferably BioDur® CCM Plus® Alloy available from Carpenter Specialty Alloys, Carpenter Technology Corporation of Wyomissing, Pa. In some embodiments, the fusion device housing components are coated with a sintered beadcoating, preferably Porocoat™, available from DePuy Orthopaedics of Warsaw, Ind.

In some embodiments, the fusion device housing is made from a composite comprising carbon fiber. Composites comprising carbon fiber are advantageous in that they typically have a strength and stiffness that is superior to neat polymer materials such as a polyarylethyl ketone PAEK. In some embodiments, the fusion device housing is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

In general, the housing is typically filled with at least one bone forming agent (BFA). The bone-forming agent may be:
a) a growth factor (such as an osteoinductive or angiogenic factor),
b) osteoconductive (such as a porous matrix of granules),
c) osteogenic (such as viable osteoprogenitor cells), or
d) plasmid DNA.

In some embodiments, the housing contains a liquid carrier, and the bone forming agent is soluble in the carrier.

In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1 BMP-3, BMP-2, OP-1, BMP-2A, BMP-2B, BMP-7 and BMP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are administered into the target disc space. In some embodiments, between about 1 microgram (μg) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft, xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the interbody space. Once the in situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. These tissues include, but are not limited to, hips, knee, vertebral body and iliac crest. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
 a) a first formulation comprising an acid-soluble type I collagen solution (preferably between about 1 mg/ml and about 7 mg/ml collagen) and
 b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or bone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In all cases, excess bone marrow aspirate can be collected and mixed with added graft extenders including collagen like the HEALOS™, INJECTOS™ and HEALOS FX™, each of which is available from DePuy Spine Inc, Raynham, Mass., USA.

Although the present invention has been described with reference to its preferred embodiments, those skillful in the art will recognize changes that may be made in form and structure which do not depart from the spirit of the invention.

We Claim:

1. A surgical method, comprising:
    inserting a fusion cage into an intervertebral disc space of a patient defined between upper and lower vertebrae, the cage having an upper surface comprising a first throughhole therethrough, a lower surface comprising a second throughhole therethrough, and a sidewall connecting the upper and lower surfaces, the sidewall comprising a third throughhole therethrough, the cage having a porous matrix therein;
    fluidly connecting an aspirator to the third throughhole; and
    creating suction in the aspirator to draw marrow from at least one of the upper and lower vertebrae, through at least one of the upper and lower surfaces, and into the cage, at least a portion of the marrow being retained within the cage by the porous matrix,
    wherein the upper surface and the lower surface include a compressible seal that lines at least one of the first and second throughholes, and
    wherein the marrow is drawn through cannulated teeth that extend from the compressible seal that lines at least one of the first and second throughholes.

2. The method of claim 1, further comprising orienting the cage such that the upper surface abuts the upper vertebra and the lower surface abuts the lower vertebra.

3. The method of claim 1, further comprising monitoring a pressure created by the suction and shutting down the suction once a pressure threshold is reached within the cage.

4. The method of claim 1, further comprising collecting marrow within the aspirator and injecting marrow collected within the aspirator back into the cage to retain stem cells of the marrow within the porous matrix.

5. The method of claim 1, wherein the upper and lower surfaces of the cage are beveled.

6. The method of claim 1, further comprising wrapping the cage with a sheath to retain suction produced by the aspirator.

7. The method of claim 1, wherein the aspirator is a syringe.

8. The method of claim 1, further comprising manipulating the cage in situ to decorticate endplates of the upper and lower vertebrae.

9. The method of claim 1, further comprising circulating material through inflow and outflow ports of the cage.

10. The method of claim 1, wherein a portion of the third throughhole is threaded.

11. A surgical method, comprising:
    creating an approach to a disc space within a patient;
    inserting a fusion cage into the disc space, the fusion cage having a first porous endplate, a second, opposite porous endplate, and a sidewall connecting the first and second endplates, the sidewall comprising an aspiration port; and
    coupling an aspirator to the aspiration port to aspirate marrow into the fusion cage from bony structures adjacent to the disc space, at least a portion of the marrow being retained by the fusion cage within the disc space,
    wherein the fusion cage includes a compressible seal that lines one or more of the first and second endplates, and
    wherein the marrow is drawn through cannulated teeth that extend from the compressible seal that lines at least one of the first and second endplates.

12. The method of claim 11, further comprising filling the fusion cage with a graft material.

13. The method of claim 12, wherein the graft material comprises one or more of a porous matrix, a bone substitute, an inorganic bone, and an expandable gel.

14. The method of claim 11, further comprising debriding the disc space prior to inserting the fusion cage therein.

15. The method of claim 11, further comprising attaching a sheath over the cage to maintain suction produced by the aspirator within the cage.

16. The method of claim 11, wherein one or more of the first and second endplates further comprises teeth for coupling to the adjacent bony structures.

* * * * *